United States Patent [19]

Bills et al.

[11] Patent Number: 5,284,758

[45] Date of Patent: Feb. 8, 1994

[54] PROCESS FOR FORMING CHOLESTEROL LOWERING COMPOUND USING PSEUDODIPLODIA SP.

[75] Inventors: Gerald F. Bills, Roselle; Mary N. Omstead, Gladstone, both of N.J.; Wendy H. Clapp, New York, N.Y.; Fernando Pelaez, Camino Valderribas, Spain

[73] Assignee: Merck & Co., Inc., Rahway, N.J.

[21] Appl. No.: 929,236

[22] Filed: Aug. 14, 1992

[51] Int. Cl.$^5$ .................. C12P 17/18; C12N 1/14; A01N 63/00; A61K 37/00

[52] U.S. Cl. ................. 435/119; 435/254.1; 424/93 Q

[58] Field of Search .............. 435/119, 254; 424/93 Q

[56] References Cited

U.S. PATENT DOCUMENTS

| | | |
|---|---|---|
| 5,026,554 | 6/1991 | Bartizal et al. . |
| 5,053,425 | 10/1991 | Bartizal et al. .................. 514/452 |
| 5,096,923 | 3/1992 | Bergstrom ..................... 514/452 |
| 5,102,907 | 4/1992 | Bergstrom et al. . |

Primary Examiner—Douglas W. Robinson
Assistant Examiner—Jeffrey J. Sevigny
Attorney, Agent, or Firm—Catherine A. Dolan; Melvin Winokur; Paul D. Matukaitis

[57] ABSTRACT

This invention relates to a fungal microorganism Pseudodiplodia sp. (MF5767) isolated from bark discs of Hibiscus sp. and useful in a fermentation process to form compounds of formula (I):

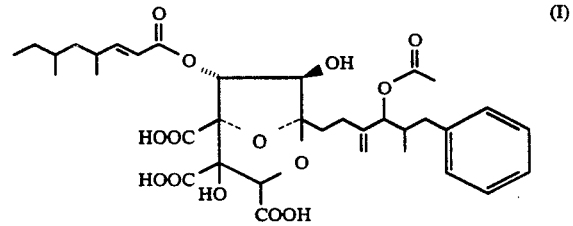

which are squalene synthetase inhibitors and thus useful as cholesterol lowering agents.

2 Claims, No Drawings

PROCESS FOR FORMING CHOLESTEROL LOWERING COMPOUND USING PSEUDODIPLODIA SP.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR ® (lovastatin) and ZOCOR ® (simvastatin), now commercially available, are members of a group of very active antihypercholesterolemic agents that function by limiting cholesterol biosyhthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol, and isopentyl t-RNA.

Previous efforts at inhibiting squalene synthetase have employed pyrophosphate or pyrophosphate analog containing compounds such as those described in P. Ortiz de Montellano et al. *J. Med. Chem.* 20. 243 (1977) and E.J. Corey and R. Volante, *J. Am. Chem. Soc.*, 98, 1291 (1976). S. Biller (U.S. Pat. No. 4,871,721 describes idoprenoid (phospinylmethyl) phosphonates as inhibitors of squalene synthetase.

Recently certain nonphosphorous containing inhibitors of squalene synthetase have been isolated as natural products. The compound of formula (I) and its use as a cholesterol lowering agent and antifungal agent is described in U.S. Pat. Nos. 5,096,923 issued Mar. 17, 1992, and 5,053,425 issued Oct. 1, 1991. These patents disclose preparation of compound (I) by an aerobic fermentation procedure employing a fungal culture MF5453 (ATCC 20986). MF5453 is an unidentified sterile fungus isolated from a water sample obtained from the Jalon river in Zaragoza, Spain.

The fungal culture of the present invention (i.e., MF5767) is a previously unknown endophytic strain of Pseudodiplodia sr. isolated from bark of Hibiscus sp.

DETAILED DESCRIPTION OF THE INVENTION

The present invention is directed to a novel microorganism that produces compounds of structural formula (I) that are squalene synthetase inhibitors:

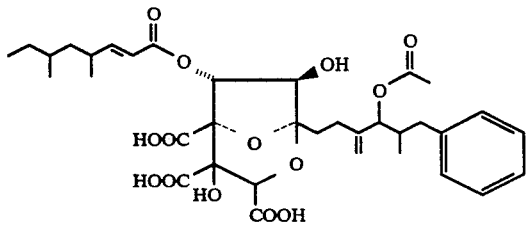

One embodiment of the present invention is the process for making compounds of formula (I) by employing strains of pseudodiplodia sp. More particularly, the novel fungal culture MF5767, a previously unknown strain of Pseudodiplodia sp., is employed. Although the use of this microorganism is specifically described herein, mutants of MF5767 are also capable of producing compounds of this invention. These mutants have essentially the same characteristics as MF5767. The term "mutant" refers to an MF5767 organism in which some gene of the genome is modified, leaving the gene or genes responsible for the organism's ability to produce compounds of formula (I) in recoverable amounts functional and heritable.

Another embodiment of the present invention is the previously unknown strain of Pseudodiplodia sp. MF5767 (ATCC 74168) or an active mutant thereof. A biologically pure culture of Pseudodiplodia sp., as claimed herein, is defined as being originally isolated from the natural environment and free of viable contaminating microorganisms. A culture of Pseudodiplodia sp., as claimed herein, is defined as being originally isolated from the natural environment and free of viable contaminating microorganisms that would be deleterious to the formation of a compound of formula (I).

The culture of MF5767 is that of an endophytic fungus, Pseudodiplodia sp. from the bark of a Hibiscus sp. collected at Mombasa, Kenya. This culture has been deposited with the American Type Culture Collection at 12301 Parklawn Drive, Rockville, Md. 20852 as ATCC 74168 under conditions of the Budapest Treaty.

The fungus emerged from the interior of healthy bark tissue after the bark was surface sterilized with 95% ethanol and a sodium hypochlorite solution to eliminate surface fungi. After incubation on selective media, the fungus emerged from the internal bark tissues and was aseptically transferred to fresh medium prior to fermentation.

The microorganism MF5767, identified as a new strain of Pseudodiplodia sp., exhibits the following morphological characteristics:

Colonies 25-26 mm in diameter after 2 weeks on yeast malt extract agar (YM agar, Difco) at 25° C., 12 hour photoperiod. Cottony to felty aerial mycelium, slightly raised, with margin even and slightly submerged, azonate. Colony color dull, gray to olivaceous gray or yellowish gray, Olive-Gray (capitalized color names from Ridgway, R., *Color Standards and Nomenclature*, Washington, D.C. 1912),. Light Grayish Olive, Deep Olive Buff, Olive Buff, Pale Olive-Buff, or pale yellow at the margin. Reverse dull grayish brown to brownish yellow, Buffy Brown, Chamois, Deep Colonial Buff, with limited conidomata formation beneath aerial hyphae. Odors and exudates absent.

Colonies 25-27 mm in diameter on Emerson Yp Ss (Difco) agar after 2 weeks at 25° C., 12 hour photoperiod. Colonies predominantly appressed, with scant, downy aerial mycelium, with abundant conidomatal development, with conidomata arranged in conspicuous concentric zones. Translucent to pale olivaceous gray, Pale Olive Gray, Light Olive Gray, with dark brownish black to black zones of :onidiomata. Odors and exudates absent.

Colonies 28-30 mm in diameter in 2 weeks on corn meal agar (Difco) at 25° C., 12 hour photoperiod. Colonies appressed, obscurely zonate, translucent, with scattered conidiomata. Odors and exudates absent.

No growth occurred at 37° C. on yeast malt agar after 2 weeks.

Conidiomata (pycnidia) globose, subglobose, pyriform to broadly ellipsoidal, with or without a short papillate, neck, ostiolate, glabrous, 100–500 μm in diameter, dark brown to black, usually submerged in the agar or with upper one third to one-half protruding, in irregular confluent masses or concatenate chains, exuding abundant conidial masses when mature, with conidial masses moist, shiny, dark brown to black. Conidiomatal wall at textura intricata to textura epidermoideae in cross section, 2–5 cell layers thick, 15–30 μm thick. Conidiogenous enteroblastic, phialidic, cells arranged in a single layer lining the entire conidiomatal cavity, 6–10 μm in diameter, subglobose, doliiform, ampuliform, sometimes with a short lateral neck, with 1–3 conidiogenous loci, sometimes periclinal thickenings are evident at conidiogenous loci. Conidia 4.5–7.5-×2–3.5 μm, ellipsoidal to broadly ellipsoidal, smooth, thin walled, pale brown to brown in KOH, about 10–60% of the conidia have a single median septum (depending on the conidioma examined). Microsclerotia, dictyospores, or synanamorphic states absent.

In culture, this fungus lacks sexual reproductive structures. It produces abundant conidia (asexual spores) within a closed cavity of fungal tissue, Classically, these closed structures are termed "pycnidia." This type asexual reproductive structure places this isolate in the form class Coelomycetes. Following the suprageneric classification scheme proposed by Sutton (B.C. Sutton, *The Coelomycetes*, Commonwealth Mycologic Institute, Kew 1980), this strain would fall within the suborder Phialopycnidiineae because stromatic tissues are absent, the conidiomata are "pycnidia," and the conidiogenous cells are enteroblastic and phialidic. Assignment of this isolate to genus is difficult because of the large number of genera in the Phialopycnidiineae and the limits of generic concepts are often ill defined. Also, generic concepts in these fungi are often based on morphological features that must be observed when the fungus is sporulating on its host plant. Normal developmental features may not be expressed in artificial culture. However, mechanically following the diagnostic procedures of Sutton, this isolate is best assigned to the genus Pseudodiplodia. This assignment is based on the combination of dark conidia, of which a significant percentage are 1 septate, ampulliform doliiform conidiogenous cells, and thin walled, glabrous, ostiolate conidiomata. Ascochyta is similar genus from which this isolate can be distinguished by its darkly pigmented conidia; in Ascochyta the conidia are hyaline or lightly colored. The genus Phoma can be eliminated as a possibility because Phoma spp. have lightly colored conidia that are typically aseptate.

In the first embodiment of the invention, compounds of formula (I) can be obtained by culturing strains of Pseudodiolodia sp. in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like.

In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts, and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging from 0.2 to 70 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into nutrient seed medium and to obtain, sometimes through a two step process, growth of the organisms which serve as seeds in the production of the active compounds. After inoculation, the flasks are incubated with agitation at temperatures ranging from 20° to 30° C., preferably 25° to 28° C. Agitation rates may range up to 400 rpm, preferably between 200 and 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar condition but employing shorter time.

After inoculation, the fermentation production medium is incubated for 3 to 30 days, preferably 4 to 14 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 26° C. The pH of the nutrient medium suitable for producing the active compounds is in the range of 3.55 to 8.5, most preferably 5.0 to 7.5. After the appropriate period for the production of the desired compound, fermentation flasks are harvested and the active compound isolated.

The active compound may then be isolated by several methods including:

An alcoholic solvent, possibly mixed with an oxygenated solvent, such as an ester or a ketone, can be employed to extract a compound of this invention from a solid fermentation medium.

The mixture is vigorously stirred and filtered, and the filtrate is concentrated under reduced pressure. Water is added to the concentrate and the pH is adjusted with a mineral acid to between 1 and 4, most preferably between pH 1.5 and 2.5. The aqueous concentrate is then repeatedly extracted with a water immiscible oxygenated solvent. The water immiscible organic layer is removed and evaporated to dryness. The residue is then generally subjected to several separation steps such as adsorption and partition chromatography, and precipitation. For each separation step, fractions are collected and combined based on results from an assay and/or HPLC/TLC analysis.

A preferred solvent for extraction of the solid fermentation is a 1:1 mixture of methanol and 2-butanone. After concentrating the initial extract and diluting with water, the preferred partitioning solvent is dichloromethane or ethyl acetate.

For extraction of compound (I) from a liquid fermentation, an oxygenated solvent, such as an alcohol, ketone, or ester, can be used. A preferred alcoholic solvent is methanol, in which case the liquid fermentation is treated with two to four volumes of methanol and is then stirred vigorously. The mixture is then filtered and the filtrate is concentrated under reduced pressure. Water is added to the concentrate, the pH is adjusted with mineral acid to between 1 and 4, most preferrably between 1.5 and 2.5. The aqueous concentrate is then extracted repeatedly with a water immiscible oxygenated solvent or chlorohydrocarbon solvent. The water immiscible organic layer is decanted and concentrated to dryness. The residue is then further purified as described above for the evaporated organic extract from solid fermentations.

A preferred oxygenated solvent for extraction of liquid fermentations is ethyl acetate. The liquid fermentation is first adjusted with mineral acid to between pH 1 and 4. most preferrably between pH 1.5 and 2.5. The mixture is then extracted repeatedly with an oxygenated solvent such as ethyl acetate or 2-butanone. The water immiscible organic layer is decanted and concentrated to dryness. The residue is then further purified as described above for the evaporated organic extract from solid fermentations. Liquid fermentations can also be extracted with 2-butanone without acidification of broth.

The chromatographic separations may be carried out by employing conventional column chromatography with ionic or nonionic resin. Silica gel, such as that available from E. Merck, is a useful adsorbent. When silica gel is the adsorbent, an alcohol/chlorohydrocarbon/ organic acid mixture such as methanol/-chloroform/acetic acid/ water is useful as an eluant. For reverse phase chromatography, the preferred adsorbent is a C8 bonded phase silica gel, although bonded phase silica gels with longer or shorter alkyl residues are also useful. The preferred eluant for reverse phase chromatography is a mixture of acetonitrile and water buffered at a low pH, such as 0.1% phosphoric acid, or trifluoroacetic acid. Ionic resins such as Dowex-1 ($Cl^-$) or Dowex-50 ($Ca^{++}$) are also useful in the purification. Of particular utility are anion exchange resins such as BioRAD AG4×4 (formate) and Amberlyst A21 (acetate). The active compound can be precipitated out of a nonpolar solvent as the quinine salt. The preferred solvent for precipitation is diethyl ether. The active compound (I) can also be precipitated out of polar solvents, such as methanol, as the ammonium salt.

Alternatively, small scale BioRad AG4×4 anion exchange adsorption/ elution of fermentation broth extracts followed by semi preparative reverse phase chromatography is a useful method for screening for the presence of known and unknown members of the Compound (I) class. Mass spectral analysis of the desalted fractions from this separation can be used to confirm the identify of known compounds.

The composition of media employed in the following Examples are listed below:

| KF SEED MEDIUM | g/L | *Trace Elements #2 | g/L |
|---|---|---|---|
| Corn Steep Liquor | 5.0 | $FeSO_4.7H_2O$ | 1.0 |
| Tomato Paste | 40.0 | $MnSO_4.4H_2O$ | 1.0 |
| Oat Flour | 10.0 | $CuCl_2.2H_2O$ | 0.025 |
| Cerelose | 10.0 | $CaCl_2.2H_2O$ | 0.1 |
| *Trace Element #2 | 10.0 ml | $H_3BO_3$ | 0.056 |
| pH adjusted to 6.8 | | $(NH_4)_6Mo_7O_{24}.4H_2O$ | 0.019 |
| (presterile) | | $ZnSO_4.7H_2O$ | 0.2 |
| 50 mls/nonbaffled 250 mls | | dissolved in 1L 0.6N HCl | |
| Erlenmeyer flask | | | |
| autoclave 20 minutes | | | |
| (121° C., 15 psi) | | | |

| CYG 40 Production Medium | g/L |
|---|---|
| Cornmeal (yellow) | 50.0 |
| Yeast extract | 1.0 |
| Glucose | 40.0 |
| no pH adjustment | |
| 45 mls/nonbaffled 250 mls | |
| ERlenmeyer flask | |
| autoclave 20 minutes (121° C., 15 psi) | |

The following examples illustrate the preparation of compounds of formula (I) and are not to be considered as limiting the invention set forth in the claims hereto.

EXAMPLE 1

Preparation of Compound (I)

A. Culturing MF5767

Culture MF5767 was inoculated into KF seed medium using one glass scoop of the original soil tube (consisting of a mixture of spores and hyphal fragments of the culture added to sterile soil). The KF seed flask was incubated for 69 hours at 25° C., 220 rpm, 85% humidity. At the end of this incubation, 2.0 ml aliquots were aseptically transferred to each of 6 CYG 40 production medium flasks. These production flasks were then incubated at 25° C, 220 rpm on a gyrotory shaker, 85% humidity, with a fermentation cycle of 14 days. Production flasks were harvested as follows: the contents of the flasks were homogenized for 60 seconds using a handheld Biospec homogenizer (Bartlesville, Okla.) and then 45 mls of 100% methanol was added to each of three production flasks; 50 mls of methyl ethyl ketone (MEK) was added to each of the three remaining flasks. All solvent treated production flasks were then placed onto a gyrotory shaker at 220 rpm for 30 minutes. After shaking, the contents of solvent treated flasks were pooled into two separate 500 ml Erlenmeyer flasks: a methanol extracted preparation and a MEK preparation.

B. Isolation of Compound (I)

A methyl ethyl ketone extract corresponding to 10 ml of whole broth (i.e., a 10 ml aliquot of the MEK preparation from Step A above) was concentrated to dryness under a stream of nitrogen. The dry extract was redissolved by shaking and sonication in 5 ml of a solution of 6 parts acetonitrile: 4 parts 0.1 M sodium formate buffered at pH 4.5 (equilibration buffer), and the solution was extracted with 5 ml of hexanes. A 4.45 ml portion of the aqueous layer was applied to a column of BioRad AG 4-X4 (volume=0.5 ml, formate cycle) anion exchange resin. The resin was prepared as follows: BioRad AG 4-X4 (100-200 mesh, free base form) was slurried 1:1 with a solution of acetonitrile/water (6/4) and the pH adjusted to 4.5 with concentrated formic acid. One milliliter of the resin slurry was transferred to a glass column and washed with 10 ml of equilibration buffer. After loading the sample, the column was rinsed with 2.5 ml of equilibration buffer followed by 2.5 ml of acetonitrile/water (6/4). The column was eluted with 7.5 ml of a solution of 0.1 N $H_2SO_4$ in acetonitrile/water (6/4). A 7.0 ml portion of the eluant was combined with 3 mL of water and extracted with 7.5 ml of ethyl acetate. The ethyl acetate layer was then concentrated to dryness under nitrogen.

The dry ethyl acetate layer was dissolved in 1.0 ml of 0.1% $H_3PO_4$ in acetonitrile/water (75/25) and a 690 μl portion was subjected to reverse phase HPLC (Phenomenex Ultracarb 5 ODS 30, 10.0 mm ×15 cm, elution 65% acetonitrile/35% water +0.1% $H_3PO_4$, flow rate 4.0 ml/min, column temperature 40.C, Waters 990+ diode array detection, fraction size 4 ml). Fractions 8 and 9 contained Compound (I) and were pooled. The pH of the solution was adjusted to 2.0 with 1.0 N HCl and the solution was extracted with ethyl acetate. The ethyl acetate layer was separated and the solvent removed in vacuo to yield Compound (I) as a yellow residue. The identity of Compound (I) was confirmed by comparing the fast atom bombardment mass spectral data with that of an authentic sample.

What is claimed is:

1. A process for producing a compound of structure

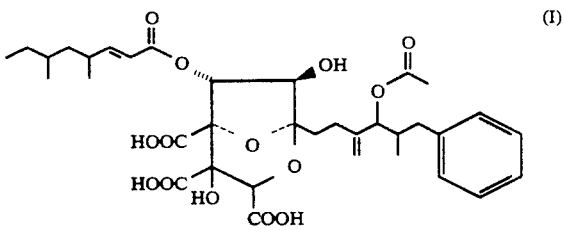

comprising cultivating Pseudodiplodia sp. ATCC 74168 or a mutant thereof capable of producing said compound under conditions suitable for formation of the compound at a temperature range of 20° to 40° C. and a pH range of 3.55 to 8.5 and recovering the compound.

2. A process of claim 1 wherein the cultivation is carrier out for 14 days.

* * * * *